United States Patent
Kruse et al.

(10) Patent No.: US 6,201,993 B1
(45) Date of Patent: Mar. 13, 2001

(54) MEDICAL DEVICE TELEMETRY RECEIVER HAVING IMPROVED NOISE DISCRIMINATION

(75) Inventors: John M. Kruse, New Brighton; David R. Jurek, Columbia Heights, both of MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/208,883

(22) Filed: Dec. 9, 1998

(51) Int. Cl.$^7$ ........................................... A61N 1/36
(52) U.S. Cl. ..................... 607/30; 607/32; 607/60; 128/903
(58) Field of Search ................... 607/30, 32, 60; 128/903

(56) References Cited

U.S. PATENT DOCUMENTS

| | | |
|---|---|---|
| 3,737,790 | 6/1973 | Brown ........................... 328/165 |
| 4,066,086 | 1/1978 | Alferness et al. . |
| 4,361,153 | 11/1982 | Slocum . |
| 4,374,382 | 2/1983 | Markowitz . |
| 4,432,360 | 2/1984 | Mumford et al. . |
| 4,531,523 | 7/1985 | Anderson . |
| 4,542,532 | 9/1985 | McQuillin . |
| 4,550,370 | 10/1985 | Baker . |
| 4,556,063 | 12/1985 | Thompson et al. . |
| 4,562,840 | 1/1986 | Batina . |
| 4,571,589 | 2/1986 | Slocum et al. . |
| 4,622,586 | 11/1986 | Megeid . |
| 4,681,111 | 7/1987 | Silvian . |
| 4,707,740 | 11/1987 | Stratton . |
| 4,809,687 | 3/1989 | Causey, III et al. . |
| 4,889,131 | * 12/1989 | Salem et al. ........................... 600/484 |
| 4,944,299 | 7/1990 | Silvian . |
| 4,947,407 | * 8/1990 | Silvian ........................... 375/94 |
| 5,058,581 | 10/1991 | Silvian . |
| 5,117,825 | 6/1992 | Grevious . |
| 5,127,404 | 7/1992 | Wyborny et al. . |
| 5,168,871 | * 12/1992 | Grevious ........................... 607/30 |
| 5,292,343 | * 3/1994 | Blanchette et al. . |
| 5,324,315 | 6/1994 | Grevious . |
| 5,354,319 | 10/1994 | Wyborny et al. . |
| 5,476,488 | * 12/1995 | Morgan et al. . |
| 5,562,713 | 10/1996 | Silvian . |
| 5,562,714 | 10/1996 | Grevious . |
| 5,617,871 | 4/1997 | Burrows . |
| 5,683,432 | * 11/1997 | Goedeke et al. . |
| 5,774,501 | * 6/1998 | Halpern et al. . |

* cited by examiner

*Primary Examiner*—Carl H. Layno
(74) *Attorney, Agent, or Firm*—Michael B. Atlass; Harold R. Patton

(57) ABSTRACT

A method and apparatus for detecting an RF signal transmitted between an implantable medical device (IMD) and an external medical device programmer in a telemetry session and discriminating the telemetry transmitted RF signal from transient and steady state noise corrupting it. The external programmer includes a programmer telemetry antenna tuned circuit adapted to be driven into oscillation to generate tuned circuit output signals in response to telemetry uplink transmissions of telemetry uplink signals from the IMD, wherein the tuned circuit output signals can exhibit noise artifacts due to contamination by electrical noise. An RF telemetry receiver section detects and demodulates the telemetry uplink signals from the tuned circuit output signals and provides a demodulated uplink signal having a demodulated uplink signal amplitude that varies with time as a function of telemetry uplink signal amplitudes and noise artifacts. The receiver section includes an adaptive comparator circuit for comparing the demodulated uplink signal amplitude with an adaptive threshold signal and providing a receiver output signal when the demodulated uplink signal amplitude exceeds the adaptive threshold amplitude of the adaptive threshold signal.

18 Claims, 8 Drawing Sheets

MEDICAL DEVICE TELEMETRY RECEIVER HAVING IMPROVED NOISE DISCRIMINATION

BACKGROUND OF THE INVENTION

1. Field of the Invention

This invention relates to a method and apparatus for detecting a radio frequency (RF) signal transmitted between an implantable medical device (IMD) and an external medical device in a telemetry session and for discriminating the transmitted RF signal from transient and steady state noise corrupting it.

2. Description of the Prior Art

In the field of programmable IMDs, it has become common to provide an interactive, transceiver system for both remotely programming operating functions, modes and parameters of the implanted device, and for telemetering out data related thereto on command by RF telemetry to an external medical device, commonly denoted a "programmer". Such IMDs include cardiac pacemakers, cardiac and other physiologic monitors, implantable drug dispensers, nerve, muscle, and brain stimulators of various types, cochlear implants, blood pumps, cardiomyostimulators, and tachyarrhythmia-control devices, e.g., implantable cardioverter/defibrillators (ICDs) for delivery of staged therapies to the ventricles and/or the atria, etc.

At the present time, both analog and digital information or data is typically transmitted by uplink RF telemetry from such IMDs to the external programmer upon receipt of a downlink telemetry interrogation command from the external programmer. The analog information has typically included battery voltage, physiologic signal amplitudes sensed in real time from sensors or sense electrodes, e.g., sampled cardiac electrocardiogram or EGM amplitude values, and, in the case of implanted pacemaker and ICD IPGs, pacing pulse and/or cardioversion shock amplitude, energy, and pulse width and lead impedance. Digital information includes digitized operating data, e.g., markers signifying device operations and data typically stored in RAM or ROM and transmitted in response to an interrogation command from such IMDs. Such stored data includes historic statistics related to device performance, episodic physiologic data stored in response to detection of an episode of interest or delivery of a therapy, e.g., cardiac electrogram segments, current programmed operating modes and parameter values, implant data, and patient and IMD identifier codes. Uplink telemetry is therefore employed to interrogate the IMD functions and memory and to confirm re-programming of operating modes and parameter values programmed in an downlink telemetry transmission.

Commonly assigned U.S. Pat. No. 5,683,432, incorporated by reference herein in its entirety, sets forth a history of the types of communication links that have been employed to communicate with an IMD, specifically including magnetic field coupling, reflected impedance coupling, and RF coupling. Static and dynamic magnetic field coupling techniques are only usable for limited programming of the IMD and have largely been abandoned, although use of static dynamic field coupling continues in the Medtronic Itrel II implantable neural stimulator. In a reflected impedance coupling system, information is transferred using the reflected impedance of an internal (implanted) L-R or L-C tuned circuit RF energized by an inductively coupled, external, L-R or L-C tuned circuit. Advantageously, such a system uses little or no current to transmit information. Disadvantageously, however, the maximum data rate of reflected impedance coupling systems is relatively slow, and the distance or rate at which information may be transferred is limited.

In RF coupled systems, which are perhaps the most commonly employed communication systems in modern implantable device systems, the RF carrier is modulated with information and is transferred from a transmitting antenna L-R or LC tuned circuit to a receiving antenna L-R or L-C circuit. Generally speaking, the modulated RF carrier induces a voltage in the receiving coil that tracks the modulated carrier signal which is then demodulated in order to recover the transmitted data. An example of a pacemaker programmer for use with programmable cardiac pacemakers having RF telemetry capabilities is disclosed in U.S. Pat. No. 4,550,370, incorporated by reference herein in its entirety.

Significant attenuation of the uplink and downlink RF telemetry signals occurs because the stainless steel or titanium canister commonly used to hermetically enclose an IMD and its antenna coil acts as a low-pass filter for the transmitted RF signals. Uplink telemetry transmission power cannot be increased to compensate for such attenuation because IMD battery power consumption must be minimized. The attenuation increases as frequency is increased, and so communications systems that are currently used have a maximum frequency of less than 200 kHz, which limits data transmission rate. Depending upon the type of modulation and demodulation used in an RF communication system, the data or bit rate cannot exceed a predetermined fraction of the carrier frequency; otherwise, the ability to reliably distinguish between modulation representing a digital (binary) "1" from a digital "0" is compromised. As a result of these constraints, the transmission range through the canister is limited to about 2–3 inches. A wide variety of proposals have been advanced in the prior art involving relocation of the telemetry antenna coil to or use of different antenna types at a location outside the canister of the IMD and use of higher frequencies in the megahertz range to increase operating range and data transmission rate but they have yet to be realized.

Since the time that such telemetry systems first became available, IMDs have proliferated in types and successive models or generations of each type that have been steadily improved in longevity and designed with increased programmable functions and capabilities. At first, in some instances, a single external programmer was designed to function with a single type or family of IMDs that could not be used to program or interrogate other IMD types or families or new generations thereof. A new programmer would have to be provided to the physicians as successive programmable IMD models and IMD functions became clinically available. In some instances, this problem was perceived and dealt with by providing the capability of upgrading the programmer so that it could communicate with the newly available IMDs and at least confirm the identity of the IMD during a programming session for safety and record keeping reasons before proceeding to the programming and interrogation functions.

Microprocessor-based programmers were developed by Medtronic, Inc. and other manufacturers which operated under the control of dedicated, plug-in ROM modules or cartridges to enable the operation of the programming and interrogation telemetry with regard to specific model or series of models of IMDs. In such systems, the programmer is incapable of communicating with a given IMD model unless the appropriate plug-in module or cartridge is first installed. For example, for many years, particular Medtronic® MemoryMod® ROM cartridges were developed and supplied to enable the physician to upgrade the programmer to program and a-interrogate a specific set of new generation Medtronic® pacemaker implantable pulse generator models.

More sophisticated, computer based programmers have been developed that is also can be upgraded, including, for example, the Medtronic® Model 9710 and 9760 programmers and the more recent Medtronic® Model 9766 and 9790 programmers which employ the Medtronic® Model 9765 programming head. It is possible to load updated software for programming new generation IMDs onto a hard disk drive from floppy disks or compact discs or through a modem and many of the other alternative ways that programs are added to personal computers, for example.

Telemetry sessions between an IMD and the external programmer are typically initiated and conducted in the manner described in commonly assigned, U.S. Pat. No. 5,168,871, incorporated herein by reference herein in its entirety. Current telemetry systems are designed to provide two-way telemetry by RF signal transmission and linkage between an antenna coil contained in the IMD canister and an antenna coil or coils contained in the programming head of the external programmer. Typically, the programming head is placed against the patient's skin overlying the IMD, and a communications link is established as depicted and described in the above-incorporated '871 patent by closure of a reed switch within the IMD by the magnetic field of a permanent magnet incorporated into the programming head. Uplink telemetry of analog and digital data of the IMD and downlink telemetry of programming and interrogation commands to the IMD is conducted in a telemetry session according to a telemetry format that is related to the particular IMD.

The RF carrier signal is modulated with the data that is to be transmitted using a particular modulation or encoding scheme employed in RF communications. Such modulation or encoding schemes include FM and AM, phase shift keying (PSK), frequency shift keying (FSK), biphasic frequency shift keying (BPSK) amplitude shift keying (ASK), pulse position modulation (PPM), pulse interval modulation (PIM), among numerous others.

An extensive description of the historical development of uplink and downlink telemetry transmission formats and pulse encoding schemes are set forth in the following series of commonly assigned patents, all of which are incorporated by reference herein in their entireties. An example of a PIM telemetry scheme used for transmitting analog and digital data as binary "1" and "0" encoded intervals between successive RF pulses from an implanted pacemaker to a remote programmer is disclosed in commonly assigned U.S. Pat. No. 4,556,063. An example of a PWM telemetry system for transmitting binary "1" and "0" encoded RF pulse widths from an implanted cardiac pacemaker to an external programmer is described in U.S. Pat. No. 4,571,589. Commonly assigned U.S. Pat. No. 5,127,404 sets forth an improved method of frame based, PPM encoded data particularly for uplink telemetry to transmit more data per unit time and reduce implanted device current drain. The frame-based PPM telemetry format increases bandwidth well above simple PIM or PWM binary bit stream transmissions and thereby conserves energy of the IMD. Various PSK, FSK, BPSK, and ASK encoding schemes are described in the aboveincorporated '432 patent or in U.S. Pat. No. 4,698,111.

Commonly assigned U.S. Pat. No. 5,168,871 sets forth an improvement in the telemetry system of the '404 patent for detecting uplink telemetry RF pulse bursts that are corrupted in a noisy environment. U.S. Pat. No. 5,292,343 sets forth a further improvement in the telemetry system of the '404 patent employing a hand shake protocol for maintaining the communications link between the external programmer and the IMD despite instability in the programmer programming head. U.S. Pat. No. 5,324,315 sets forth an improvement in the uplink telemetry system of the '404 patent for providing feedback to the programmer to aid in optimally positioning the programmer programming head over the IMD. U.S. Pat. No. 5,117,825 sets forth an further improvement in the programmer programming head for regulating the output level of the magnetic, H field of the programming head telemetry antenna using a signal induced in a sense coil in a feedback loop to control gain of an amplifier driving the programming head telemetry antenna. U.S. Pat. No. 5,562,714 sets forth a further solution to the regulation of the output level of the magnetic, H field generated by the programming head telemetry antenna using the sense coil current to directly load the H field. U.S. Pat. No. 5,354,319 sets forth a number of further improvements in the frame based telemetry system of the '404 patent. U.S. Pat. No. 5,683,432 sets forth a communication system that dynamically adjusts operational parameters of the communication link during a telemetry session between an IMD and an external programmer.

Many of these improvements have been incorporated into current generation programmers which can be operated to program and interrogate long-lived IMDs that may be several generations old while also programming the most currently implanted generations of a wide variety of IMD types and families.

To ensure the safety of the patient, telemetry systems have been designed conservatively to avoid mis-programming or corruption of uplink telemetry data once acquisition has been obtained. The presence of electrical interference or noise strong enough to interrupt reception of telemetry from the external programmer can affect operation of uplink and downlink telemetry functions, including proper programming and interrogation. The programming and interrogation of IMDs typically takes place in hospital operating rooms, cauterization laboratories and physicians' offices which are often noisy electrical environments, and such noise has been found on occasion to interfere with the proper programming or interrogation of an IMD.

The programming heads used with the above-referenced Medtronic® Model 9710, 9760, and 9766 programmers, e.g., the Model 9765 programming head, employ antenna circuitry of the type described in commonly assigned U.S. Pat. No. 4,542,532, incorporated by reference herein in its entirety and in the above-incorporated '871 patent. The programming heads incorporate dual antenna coils tuned to 175 kHz center frequency to reject far-field noise which tends to link both coils with the same field strength. As explained in the '532 patent, the two antenna coils are wound in series opposition in the receive mode, and therefore, the noise field component from the remote noise source should be canceled, leaving primarily the signal component at the input of the receiver bandpass filter. However, noise is not always canceled in this manner, and it must be dealt with in the uplink telemetry receiver section of the programming head transceiver circuitry.

In one early approach, the signal output by the tuned in the receiver circuitry is bandpass filtered and processed using a manual gain control circuit. The use of automatic gain control (AGC) circuitry is disclosed in U.S. Pat. No. 4,562,840 and software implemented gain control circuitry is disclosed in U.S. Pat. No. 4,531,523, both incorporated by reference herein in their entireties. The gain of an amplification stage is attempted to be optimized to minimize mistaking noise and electrical interference for an uplink telemetry RF signal (characterized as a "false positive" response) and to avoid failing to pick up an actual uplink telemetry RF signal that is masked by such noise or interference (characterized as a "false negative" response).

These approaches do not completely eliminate false positive and false negative responses from occurring. Further improvements in the programming head receiver circuitry attempting to diminish these responses are disclosed in the above-incorporated '871 patent and were implemented into the Model 9765 programming head. In the '871 patent, the telemetry receiver section is coupled to a tuned circuit of the type described in the above-incorporated '532 patent, deliberately tuned outside the pulse frequency pass band. The receiver section bandpass filters and amplifies the signal output by the tuned circuit in response to RF signals and electrical noise or interference. Then, the filtered and amplified signal is applied to a detector block 124 incorporating signal phase shifting and mixing blocks. The phase shifting and mixing blocks invert positive polarity transient noise artifacts in the detector output signal applied to the carrier filter to reduce false positive response to positive polarity transient noise artifacts. The signal output by the detector block 124 is applied to a carrier filter block 130 that attenuates noise signals and artifacts and provides a demodulated uplink pulse signal that is then applied to an output comparator block 134 for comparison to a fixed reference voltage. The output comparator block 134 in the '871 patent compares the positive going demodulated uplink pulse signal with a fixed comparator threshold voltage that is set to 1.16 volts to provide the RCVTLM output signal to the programmer when the demodulated uplink pulse signal exceeds the threshold voltage. This relatively low threshold level is chosen to optimize overall performance by taking advantage of the characteristically clean base line of the receiver design. Under transient noise conditions, the detector block provides good suppression of false positive responses, but does not avoid false negative responses to actual uplink telemetry RF pulses. When a transient noise burst occurs coincident with an uplink telemetry RF burst, the phase relationship of the two signals will determine whether the amplitude of the positive going output signal (nominally 5.0 volts for the peak RF pulse) will be enhanced or degraded. The relatively low 1.16 volt comparator threshold provides added margin against false negative responses and is set at the level where both the false negatives and false positives begin to occur simultaneously for very large transient input noise levels, thereby optimizing overall receiver performance. However, the low amplitude comparator threshold is more likely to allow provide a false positive response if noise is not attenuated sufficiently by the detector block.

The comparator 134 also operates in a manner similar to a "slicer" commonly used in AM and FM signal demodulation that extracts analog signals from noise signals and converts the analog signals into a digital signal suitable for further processing by standard low voltage processing circuits. Programmer receivers that disclose use of an AM or FM "slicer" for analog to digital conversion of the analog signal are also shown in the above-incorporated '111 patent. In the '111 patent, the "slicer" simply comprises an op amp with feedback to provide hysteresis that compares the input signal to ground potential and provides a squared "binary" output signal.

These approaches do not solve all the false positive and false negative response problems due to noise in the signal output by the tuned circuit. At present, it is still necessary to hold the programming head as close to the IMD as possible and to maintain it very steady during the telemetry session to successfully telemetering data and commands between an IMD and an external programmer of the types described above. The uplink telemetry signal strength decreases exponentially with distance, and, consequently, noise levels become problematic as distance is increased. Moreover, the noise amplitude can vary considerably from moment to moment. In spite of these problems, it is a goal to be able to expand the coupling distance between the antenna coils in the IMD and the programming head, which necessarily reduces signal strength, while maintaining adequate noise discrimination. A primary reason for increasing the coupling distance is so that the programming head can be located out of the sterile field during an implantation of an IMD.

In addition, the uplink telemetry fidelity demands continue to steadily increase as the amount of uplink telemetered data is increased and as a greater variety of IMD types and models of any single type become available. The uplink telemetry signals output by these IMDs differ in type, frequency, pulse width and amplitude, modulation codes, etc., from manufacturer to manufacturer and sometimes between IMDs of differing models or types offered by the same manufacturer. As described above, considerable effort has been expended by manufacturers over the years to ensure at least that their current programmers operate with a wide range of both current and predecessor IMDs offered by that manufacturer. It is also desired to be able to make the programmer transceiver circuitry capable of accurately detecting a wide variety of uplink telemetry signals while avoiding or minimizing the false negative and false positive responses in the presence of electrical noise or interference.

Consequently, a need remains for further discriminating telemetry RF signals from noise and interference while expanding the capability of the telemetry system to operate with a wide variety of IMDs and increasing volumes of telemetered signals while relaxing the close and steady spacing requirements between the IMD antenna and the programmer antenna.

SUMMARY OF THE INVENTION

It is an object of the invention or inventions descried in detail below, to solve the at least some of the problems identified with prior art telemetry systems for communicating between an external programmer and an IMD.

Preferably also, the present invention to improve a receiver section of a programmer to be more sensitive to lower amplitude uplink telemetry signals in the presence of background noise.

It is still a further object of the present invention to improve the discrimination of low amplitude uplink telemetry RF signals from noise in a receiver section of a programmer.

In accordance with the present invention, the uplink telemetry signal contaminated with noise is processed through a comparator against an adaptive reference level derived from the noise and signal level to produce a comparator output signal that represents the uplink telemetry signal and thereby reduces instances of false positive response.

In one realization of the present invention, a method and apparatus for detecting an RF signal transmitted from an IMD in a telemetry uplink session to an external medical device programmer and for discriminating the uplink telemetry transmitted RF signal from transient and steady state noise corrupting is provided. The external programmer includes a programmer telemetry antenna tuned circuit including at least one antenna coil and at least one tuning capacitor, the tuned circuit adapted to be driven into oscillation to generate tuned circuit output signals in response to telemetry uplink transmissions of telemetry uplink signals and is susceptible of being driven into oscillation in response to electrical noise, whereby the tuned circuit output signals can exhibit noise artifacts due to contamination by such electrical noise. A telemetry receiver section is provided for detecting and demodulating the telemetry uplink signal from the tuned circuit output signal and providing a demodulated uplink signal having a demodulated uplink signal amplitude that varies with time as a function of the time varying telemetry uplink signal amplitude and noise artifacts. The receiver section includes an adaptive comparator circuit for comparing the demodulated uplink signal amplitude with an adaptive threshold signal derived from and representing the amplitude of noise artifacts contaminating the telemetry uplink signal. The adaptive comparator circuit provides a receiver output signal when the demodulated uplink signal amplitude exceeds the adaptive threshold signal amplitude.

More specifically, the comparator circuit also filters and integrates the demodulated uplink signal to derive the adaptive threshold amplitude that is proportional to and adapts to the instantaneous amplitude of noise artifacts in the demodulated uplink signal. The comparitor circuit has a first input terminal for receiving the demodulated uplink signal and a second input terminal for receiving the adaptive threshold signal and an output terminal. The comparison means compares the demodulated uplink signal amplitude with the adaptive threshold amplitude and provides the receiver output signal at the output terminal only when the telemetry signal amplitude in the demodulated uplink signal exceeds the adaptive threshold amplitude.

In comparison to the known programming systems, the present invention provides numerous advantages including an improved signal-to-noise ratio of 2–3 dB in comparison to the fixed reference or threshold employed in the above-incorporated '871 patent. The adaptive threshold level closely tracks the instantaneous noise level so that noise transients of any amplitude cannot exceed the threshold sufficiently to trigger a false positive response receiver output signal.

The present invention therefore provides solutions to problems of transmitting information-encoded, telemetry signals percutaneously between an IMD and an external device as uplink telemetry RF pulses contaminated with positive going and negative going noise artifacts.

The present invention can also be employed in the receiver section of the transceiver of an IMD to aid in discriminating downlink telemetry signals from background noise contaminating the downlink telemetry signals.

The information-encoded, telemetry signals transmitted from a telemetry antenna and transmitter circuit in a telemetry transmission are preferably encoded via one of the encoding schemes in the group comprising FM and AM, PSK, FSK, BPSK, ASK, PPM, or PIM.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other objects, advantages and features of the present invention will be appreciated to those of skill in the art as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION OF THE PREFERRED EMBODIMENTS

Figure 3:
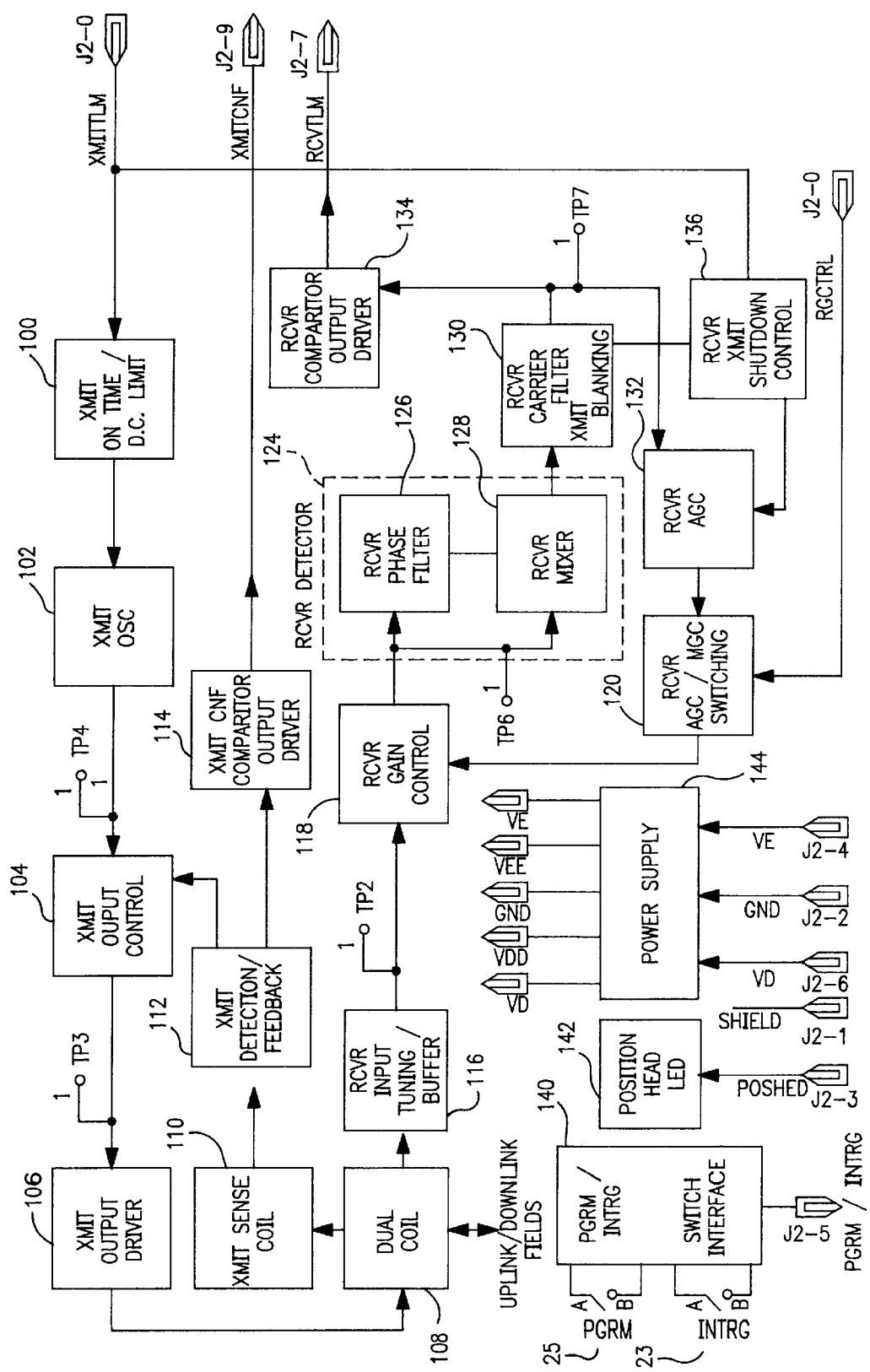
FIG. 3 is a simplified schematic diagram of the major components of the programmer programming head transmitter and receiver circuit employed in the system of FIGS. 1 and 2.
Figure 4A:
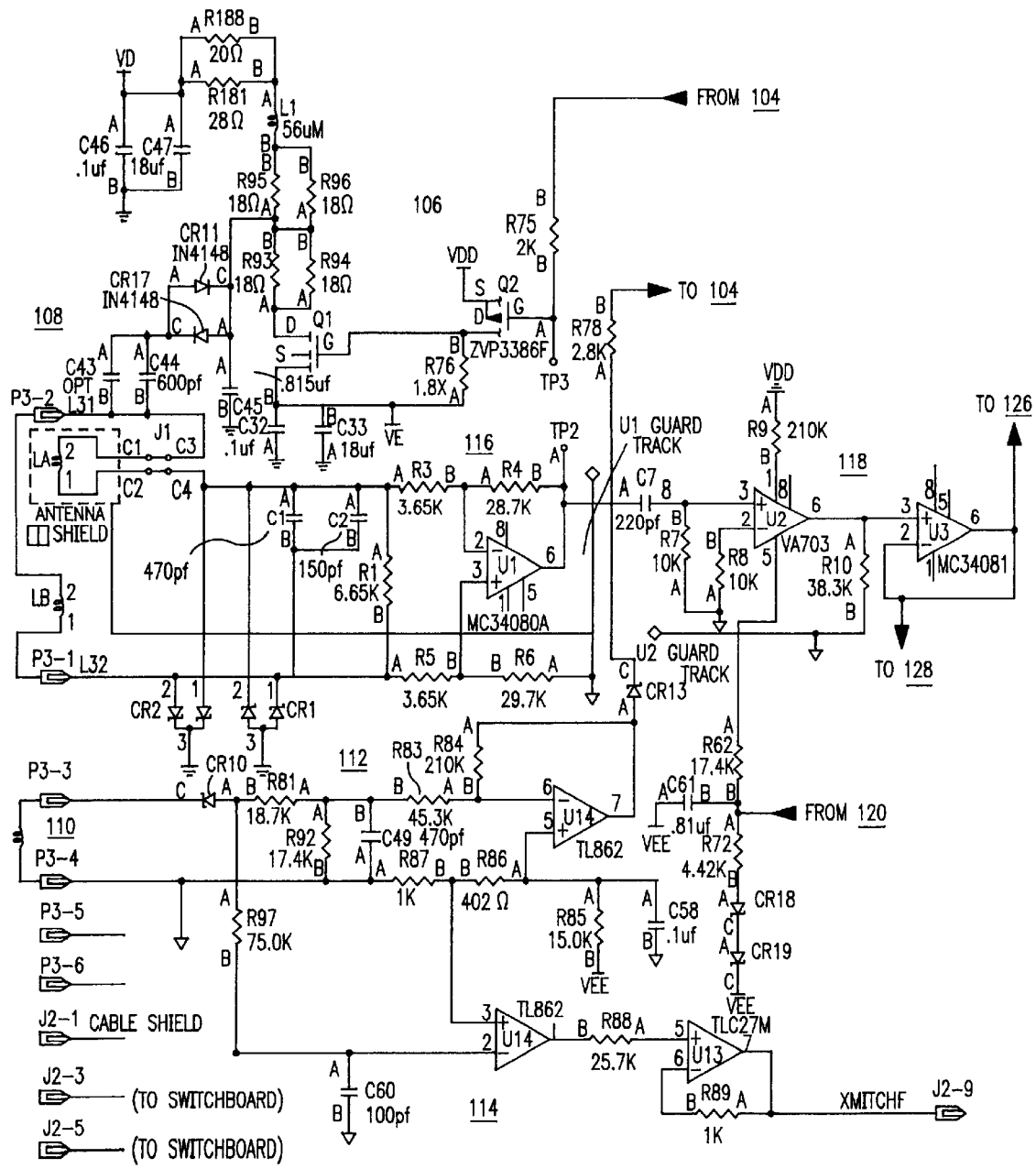
FIGS. 4A–4C is a detailed schematic diagram of the programmer programming head transmitter and receiver circuit of FIG. 3.
Figures 1, 4B:
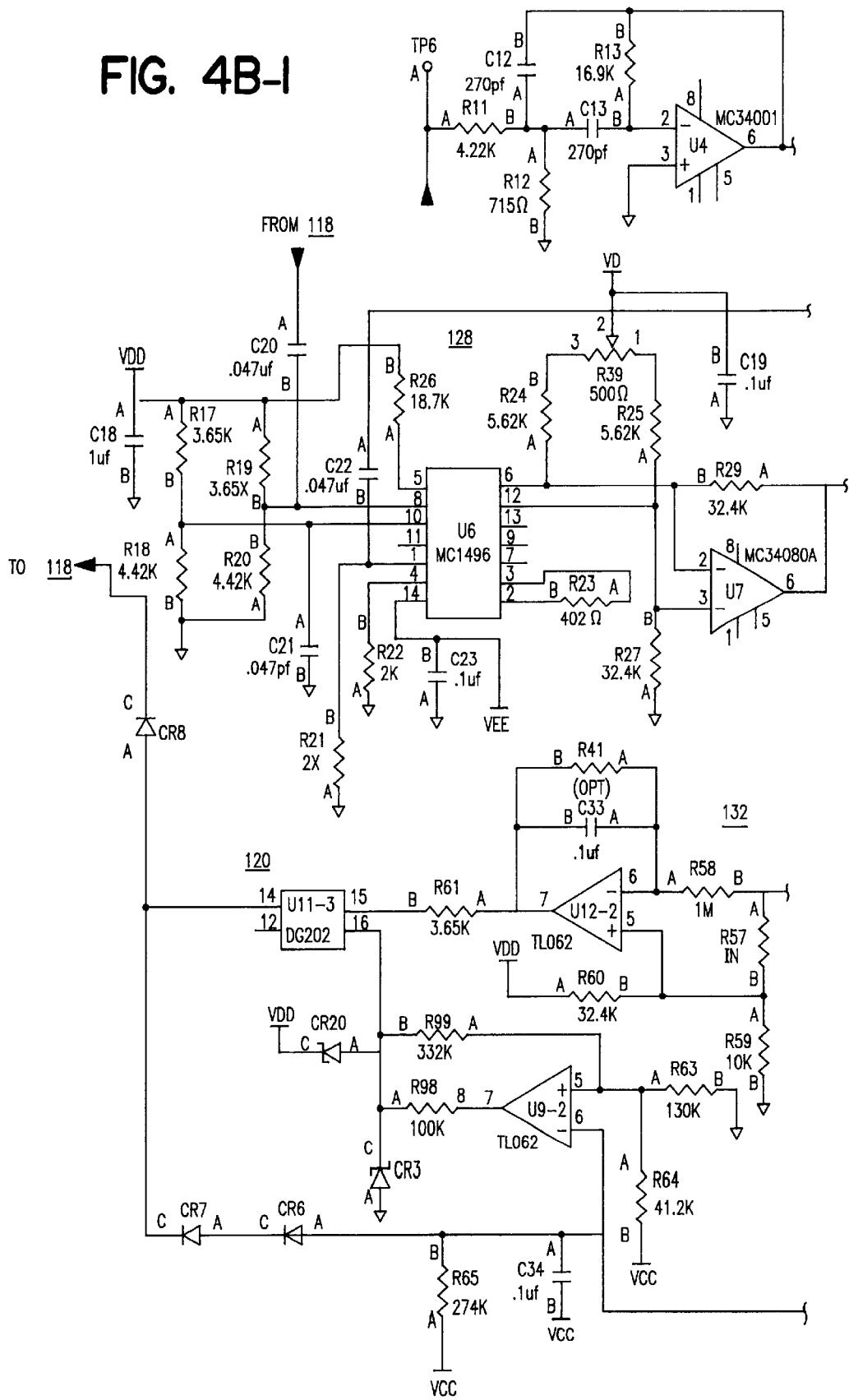
Figures 2, 4B:
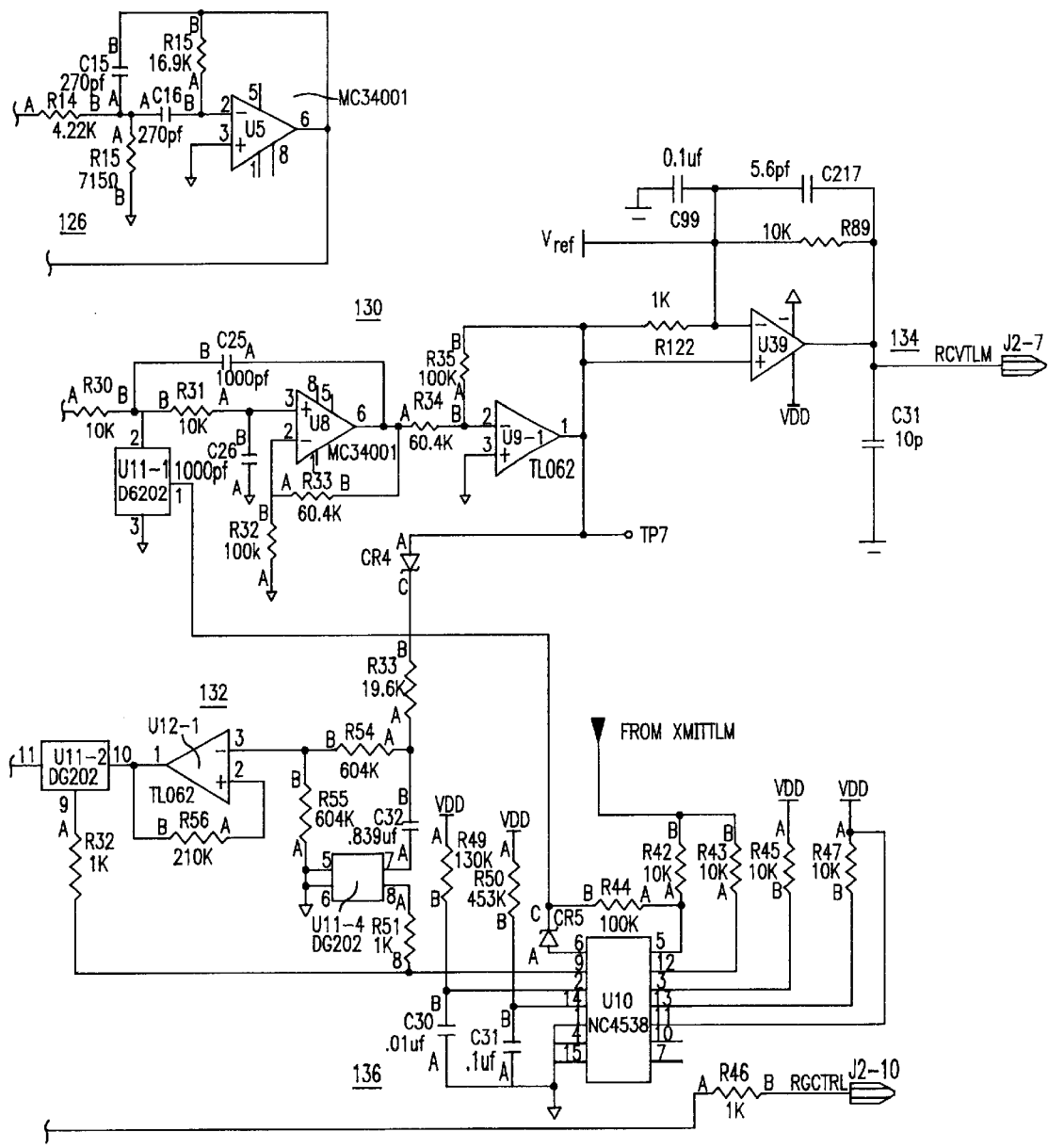
Figure 4C:
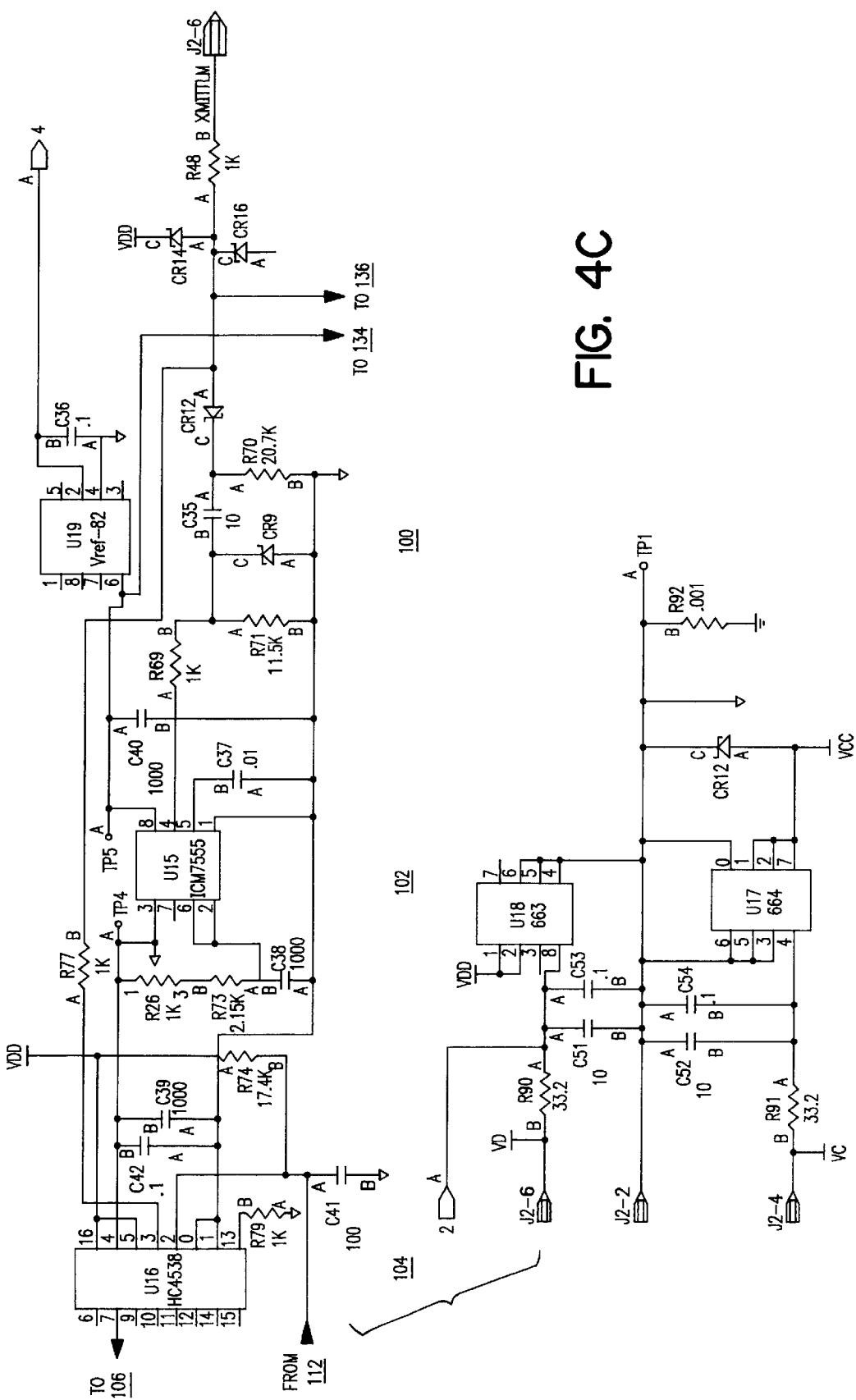
Figure 5:
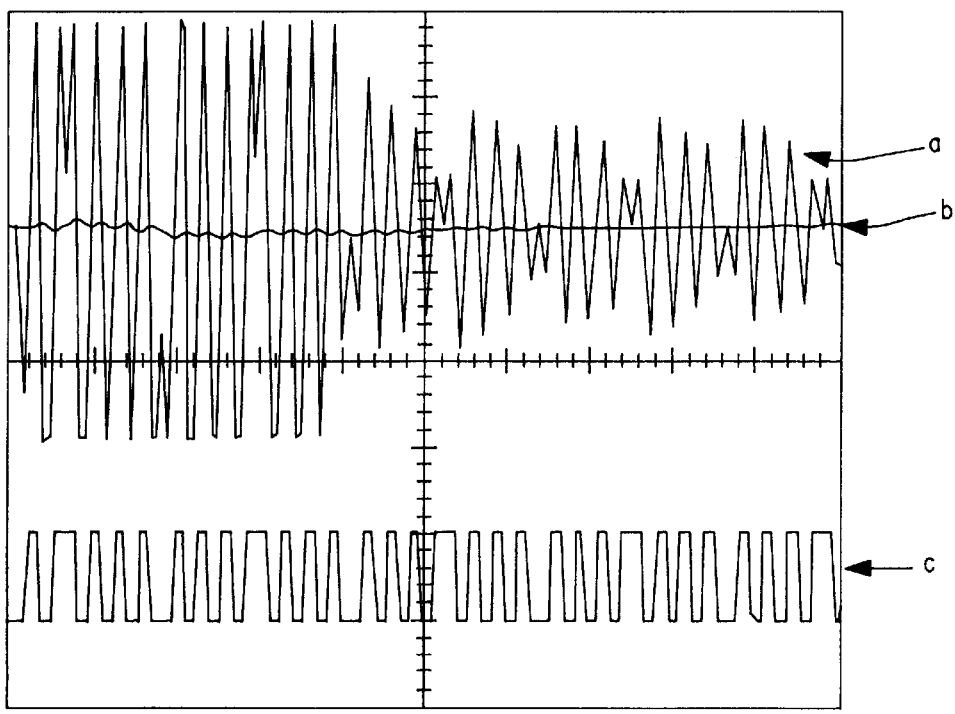
FIG. 5 is a waveform diagram displaying the operation of the adaptive comparator block of FIG. 4B-2.

It will be understood that the detector and discrimination circuitry of the present invention as depicted hereafter in conjunction with FIGS. 3–5, may be implemented in programmer head circuitry coupled through a relatively long cable to a remote programmer of the type disclosed in the above-incorporated '871 patent.

Figure 1:
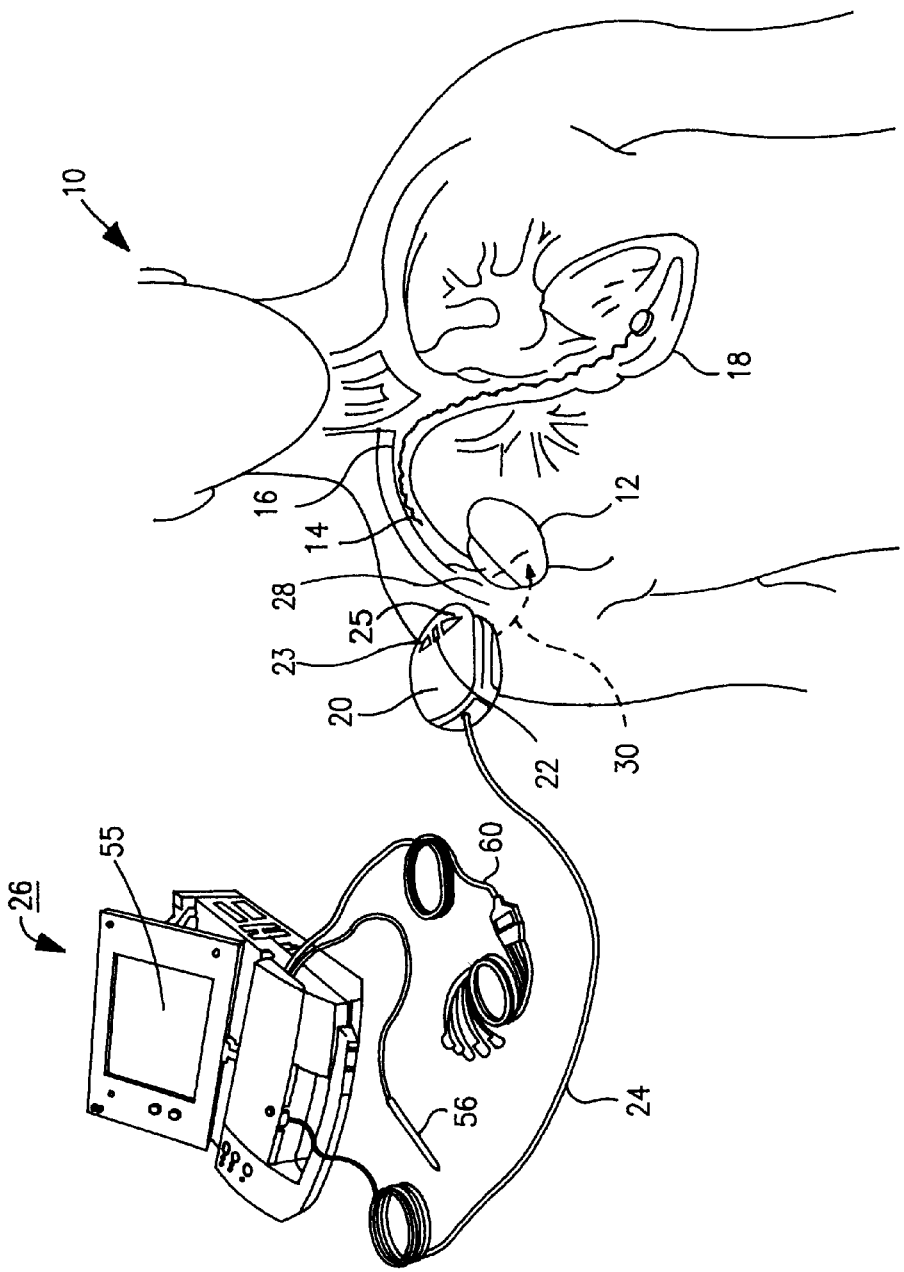
FIG. 1 is a simplified view of an IMD and external programmer embodying the improved programmer programming head and telemetry pulse generator in accordance with the present invention.

FIG. 1 is a simplified view of the bidirectional telemetry communication between an external programmer 26 and an IMD, e.g., a cardiac pacemaker implantable pulse generator (IPG) 12, employing the detector and discrimination circuitry of the present invention. As in the typical implantation of any programmable and interrogatable IMD, the IPG 12 is implanted in the patient 10 beneath the patient's skin and typically oriented to the skin surface in the manner illustrated in the aboveincorporated '714 patent. The IPG 12 can take the form of the IPG described in detail in the above-incorporated '432 patent. The IPG 12 is electrically coupled to the heart 18 of the patient 10 through pace/sense electrodes and lead conductor(s) of at least one cardiac pacing lead 14 in a manner known in the art. The IPG 12 contains an operating system that may employ a microcomputer or a digital state machine for timing sensing and pacing functions in accordance with a programmed operating mode. The IPG 12 also contains sense amplifiers for detecting cardiac signals, patient activity sensors or other physiologic sensors for sensing the need for cardiac output, and pulse generating output circuits for delivering pacing pulses under control of the operating system in a manner well known in the prior art. The operating system includes memory registers or RAM for storing a variety of programmed-in operating mode and parameter values that are used by the operating system. The memory registers or RAM may also be used for storing data compiled from sensed cardiac activity and/or relating to operating history for telemetry out on receipt of a retrieval or interrogation instruction. All of these functions and operations are well known in the art, and many are employed in other programmable, IMDs to store operating commands and data for controlling device operation and for later retrieval to diagnose device function or patient condition.

Programming commands or data are transmitted between an IPG telemetry antenna within IPG 12 and a programming head telemetry antenna within programming head 20 during a telemetry uplink transmission 28 or downlink transmission 30. In a telemetry uplink transmission 28, the programming head telemetry antenna operates as a telemetry receiver antenna, and the IPG telemetry antenna operates as a telemetry transmitter antenna. Conversely, in a telemetry downlink transmission 30, the programming head telemetry antenna operates as a telemetry transmitter antenna, and the IPG telemetry antenna operates as a telemetry receiver antenna.

As illustrated in FIGS. 3 and 4A and described in greater detail below, the telemetry antenna in programming head 20 is formed of a pair of antenna coils having coil inductances LA and LB providing a total inductance L and capacitors having a total capacitance C coupled together in an L-C tuned circuit configuration. Moreover, a transmit sense coil illustrated in FIG. 4A of the type described above is located in proximity to the programming head antenna L-C tuned circuit within programming head 20. The L-C tuned circuit and the sense coil in the hand held, programming head 20 are coupled with a transceiver, including a telemetry transmitter circuit, a telemetry receiver circuit, and an RF field sense circuit and related circuit components that are coupled through cable 24 with the programmer 56. The transmit sense coil is used during downlink telemetry to verify that an RF pulse is being transmitted and to regulate the amplitude of the H field as described in the above-incorporated '714 patent.

The magnetic field of a permanent magnet within programming head 20 closes a magnetic field sensitive reed switch in the IPG 10 when the programming head 20 is held over it a during a telemetry session as a safety feature, as taught in U.S. Pat. No. 4,006,086, incorporated by reference herein in its entirety. The programming head telemetry antenna coils and associated mechanical components in the programming head 20 of such Medtronic® programmers are designed to minimize antenna loading to achieve the highest possible antenna Q. This requires special configurations of a non-conductive or segmented permanent magnet used to close the reed switch in the IMD, antenna coil, sense coil and segmented E-shields and attention to loading by other components, e.g. the printed wiring board circuits. The resulting H field that is generated during the ringing of the antenna L-C tuned circuit is regulated in amplitude by loading effected when voltage induced in the sense coil causes breakdown diodes to conduct. This passive circuit regulates the Q by direct loading of the H field when the diodes conduct as described in the above-incorporated '714 patent.

INTERROGATE and PROGRAM push-buttons 23 and 25 and an LED display 22 are provided on the programming head 20 and are also electrically connected through electrical cable 24 to external programmer 26. The INTERROGATE and PROGRAM push-buttons 23 and 25 are provided to be selectively depressed by the medical care giver to start the telemetry uplink and downlink transmissions 28 and 30, respectively, as described in detail in the above-incorporated '871 patent. The LED display 22 is also provided that is coupled to a sense circuit in programmer 26 described above and is illuminated during a telemetry uplink or downlink transmission 28 or 30 to alert the medical person that the transmission is taking place.

An ECG cable 60 is also provided extending from programmer 26 having a plurality of ECG skin electrodes that can be placed at specified points of the patient's torso and limbs. Graphics display screen 55 is used to display the patient related data and menu choices and data entry fields used during telemetry uplink and downlink transmissions 28 and 30. A user of programmer 26 interacts therewith by touching stylus 56 against a selected location on screen 55 which displays the appropriate menu choices. Other components within the programmer console are described below with reference to FIG. 2.

In use, the attending medical care giver applies the ECG skin electrodes to the patient's body and/or holds programming head 20 against the patient's skin and over the IPG 12 to align the transceiver antennas in each as close together and as still as possible to ensure reliable telemetry transmission during the time that it takes to complete a telemetry uplink or downlink transmission 28 or 30. As described in detail in the above-incorporated '714 and '871 patents, the loading and tuning, and therefore the impedance, of the programming head telemetry antenna is affected by the proximity of the programming head telemetry antenna and the IPG telemetry antenna. Any movement can change the strength of the electromagnetic field between the two antennas during either a telemetry uplink or a downlink transmission 28 or 30 and change the strength of the signal induced by the field in the telemetry receiver antenna coils in the programming head 20.

Both the IPG 12 and the programming head 20 include transceiver circuits that each comprise a transmitter section and a receiver section coupled with antenna coil L-C tuned circuits. The adaptive comparator circuit of the present invention can be employed in either context, and will be specifically described hereafter in the context of the programming head 20.

Figure 2:
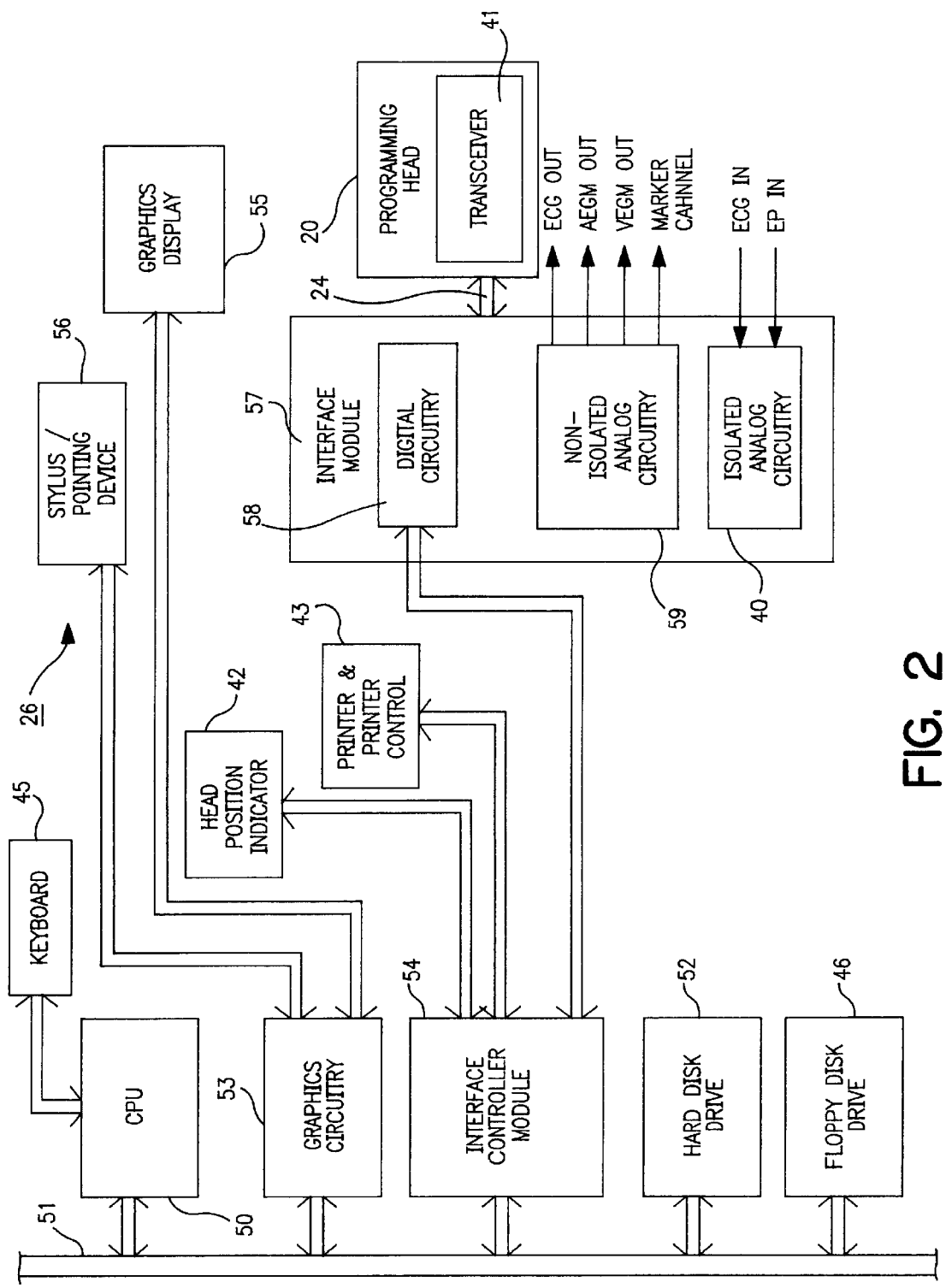
FIG. 2 is a simplified circuit block diagram of major functional blocks of the external programmer of FIG. 1.

A simplified block diagram of an exemplary programmer 26 in which the present invention may be implemented is set forth in FIG. 2 and is based upon the above-referenced Medtronice Model 9760 or 9790 programmer or preferably the Model 9790 programmer that is depicted and described in the above-incorporated '432 patent. Programmer 26 is a personal computer type, microprocessor-based device incorporating a central processing unit 50, which may be, for example, an Intel 80386 or 80486 or Pentium microprocessor or the like. A system bus 51 interconnects CPU 50 with a hard disk drive 52 storing operational programs and data and with a graphics circuit 53 and an interface controller module 54. A floppy disk drive 36 (or a CD ROM drive) is also coupled to bus 51 and is accessible via a disk insertion slot (not shown) within the housing of the programmer 26. Programmer 26 further comprises an interface module 57 which includes digital circuit 58, non-isolated analog circuit 59, and isolated analog circuit 40. Digital circuit 58 enables interface module 57 to communicate with interface controller module 54.

An alphanumeric keyboard 45 for entering text or numbers and other symbols is optionally provided to allow the medical person to communicate with CPU 50 in the programmer 26. However, the primary user communication mode is through graphics display screen 55 of the well-known "touch sensitive" type controlled by graphics circuit 53 and a stylus 56 coupled thereto. As noted above, graphics display screen 55 is used to display the patient related data and menu choices and data entry fields used during telemetry uplink and downlink transmissions 28 and 30. A user of programmer 26 interacts therewith by touching stylus 56 against a selected location on screen 55 which displays the appropriate menu choices.

Graphics display 55 also displays a variety of screens of telemetered out data or real time data. Programmer 26 is also provided with a strip chart printer 63 or the like coupled to interface controller module 54 so that a hard copy of a patient's ECG, atrial and/or ventricular electrogram (AEGM, VEGM), Marker Channel or of graphics displayed on the display 55 can be generated.

The transceiver circuitry 41 is connected to the interface module 57 of the external programmer 26 via conductors in an elongated electrical cable 24. During a telemetry uplink transmission 30, the telemetry receiver circuit in transceiver 41 is enabled. The telemetered out RF pulses of the uplink transmission 30 are detected, demodulated, decoded and applied to the digital circuit 58 to be digitized and recorded in RAM or in a hard or floppy disk or the like. The digitized data may be contemporaneously or later retrieved from memory and displayed on graphics display screen 55 or printed out for the attending medical personnel.

The analog and ventricular channel EGM signals from atrial and ventricular pace/sense electrodes may be digitized within IPG 12 and uplink telemetered to programmer 26 on receipt of a suitable INTERROGATE command. The uplink transmission 28 of the telemetered EGM signals are received in programming head 20 and provided to non-isolated analog circuit 59. Non-isolated analog circuit 59, in turn, convert the digitized EGM signals to analog EGM signals (as with a digital-toanalog converter, for example) and presents these signals on output lines designated in FIG. 2 as AEGM OUT and VEGM OUT. These output lines may then be applied to a separate strip-chart recorder or the like to provide a hard-copy printout of the AEGM or VEGM signals transmitted from I PG 12 for viewing by the physician.

The IPG 12 may also be capable of generating so-called marker codes indicative of different cardiac events that it detects. An IPG with Marker Channel capability is described, for example, in commonly assigned U.S. Pat. No. 4,374,382, incorporated by reference herein in its entirety. The markers provided by IPG 12 may be received by programming head 20 and presented on the MARKER CHANNEL output line from non-isolated analog circuit 59.

Isolated analog circuit 40 in interface module 57 is provided to receive external ECG and electrophysiologic (EP) stimulation pulse signals. In particular, analog circuit 40 receives ECG signals from patient skin electrodes of ECG cable 60 and processes these signals before providing them to the remainder of the programmer system in a manner well known in the art. Isolated analog circuit 40 further operates to receive the EP stimulation pulses from an external EP stimulator for the purposes of non-invasive EP studies, as is also known in the art.

To initiate a telemetry uplink transmission 28, the telemetry transmitter in transceiver 41 is enabled in response to depression of the INTERROGATE pushbutton to generate an INTERROGATE RF pulse command that first initiates a downlink telemetry transmission 30 of a series of RF pulses. Each RF pulse of the instruction or command that is transmitted causes the IPG L-C tuned circuit to ring. The train of induced voltages is detected and decoded by the receiver circuit in the IPG transceiver. After the command or instruction is decoded, the stored data to be uplink transmitted is encoded into PPM modulated RF pulses in data frames. The methods and apparatus for formatting such uplink data frames for Medtronice IPGs and other IMDs are set forth in detail in the above-incorporated '404, '319 and '343 patents. The transmitter circuit in the IPG transceiver applies voltage to the IPG RF antenna causing the L-C tuned circuit to ring and generate the uplink RF pulses which induce signals in the programming head telemetry antenna. The induced signals are detected in the telemetry receiver circuit in transceiver 41 and applied as a pulse train on cable 24 to interface module 57 where the frame of a series of such signals is decoded so that the data can be recorded or displayed as described above.

The downlink telemetry RF pulse bursts generated in the Medtronic® telemetry formats are relatively constant in frequency and pulse width due to the characteristics of the programmer programming head telemetry antenna and the frequency at which it is driven. A fixed interval telemetry transmit telemetry (XMITTLM) pulse is applied to the programmer telemetry transmitter circuit which drives an oscillating signal into the programming head telemetry antenna coils having an inductance L and a capacitor or capacitors having a capacitance C. The antenna L-C tuned circuit is tuned in its connection with a receiver circuit to resonate in response to a transient signal (e.g. spurious noise) at about 128 kHz. However, an uplink 175 kHz signal can be detected. During downlink telemetry, the antenna L-C tuned circuit resonates and generates a burst of RF cycles at the downlink 175 kHz frequency, as described in the above-incorporated '714 and '871 patents. At the termination of the telemetry transmit pulse, the L-C tuned circuit continues to resonate as stored energy is dissipated, resulting in a series of declining amplitude, damped sinusoidal waves to a quiescent level.

In the above-referenced Medtronic® programmers and IMDs, the frame-based telemetry format is not currently employed for downlink telemetry transmissions 30. Instead, a simpler bit stream format is employed that can be used to robustly transmit INTERROGATE commands or PROGRAM instructions under the control of CPU 50. After selection of the appropriate menu choices and during depression of an INTERROGATE or PROGRAM push-button, the CPU 50 and digital circuit 58 generate XMITTLM pulses at timed intervals the PPM position of each telemetry frame. As each downlink telemetry trigger pulse for each such frame is generated, it is applied to the telemetry transmitter circuit in the transceiver 41 which responds by applying voltage to the L-C tuned circuit of the programming head telemetry antenna.

FIG. 3 depicts in block diagram form the blocks of the transceiver circuit within the programming head 20 as well as the input and output signals exchanged between the programmer central processing unit and the programming head 20 labeled at terminals J2-1 to J2-9. The terminals J-2 through J-9 are coupled to respective conductors in cable 24 that extends from the programming head 20 to the microprocessor based programmer circuitry in the programmer 26. Certain test points used in manufacturing are indicated in the figures by the "TP" designation.

The INTERROGATE and PROGRAM button switches 23 and 25, respectively, that the physician selectively depresses in FIG. 1 during interrogation and programming modes are depicted in FIG. 3 coupled to the program/interrogate switch interface block 140. The switch interface block 140 provides the respective PROGRAM or INTERROGATE command signal via terminal J2-5 and cable 24 to the central processing unit of the programmer 26. The signal that is transmitted out of block 140 back to the programmer 26 allows telemetry in (or uplink telemetry) and telemetry out (or downlink telemetry) to take place under command of data entered by the user into the programmer 26.

The block diagram of FIG. 3 includes the dual antenna coil block 108 that is coupled with the transmitter section comprising transmitter circuitry blocks 100, 102, 104, 106, 110, 112, 114 and 136 employed in downlink telemetry transmissions in the downlink telemetry mode. When the XMITTLM signal is received at terminal J2-8, it provides downlink telemetry RF signals from the dual antennae coil block 108, sends a transmit confirmation (XMITCNF) signal via terminal J2-9 back to the programmer 26, and blanks or shuts down the receiver section of the circuitry and freeze the receiver automatic gain control during downlink telemetry.

The position head LED block 142 responds to a position head input signal (POSHED) at terminal J2-3 to light up as long as the programming head is not properly positioned over the IMD and a power supply block 144. The power supply block 144 provides isolated, regulated power supplies for different portions of the transceiver circuit in order to avoid interference between the transmitting and receiving sections through either the power supply positive voltage or ground lines as shown in FIGS. 4A–4C. The fabrication of the transceiver circuit and the dual antennae coil block 108 are described in the above-incorporated '871 patent.

Returning to the transmitter section, the transmitted signal is a 175 kHz RF pulse which is keyed ON and OFF by the XMITTLM signal delivered from the programmer at terminal J2-8. The XMITTLM signal is passed through an ON-time and duty cycle limit circuit 100 before it is allowed to key the transmit (XMIT) oscillator 102 ON. The XMITTLM signal also is delivered to a transmit shutdown controller 136 located in the receiver portion. Block 136 serves to blank the receiver output of block 130 and freezes the AGC value in block 132 during transmit operation.

Valid XMITTLM signals that are able to pass through the ON-time and duty cycle limit circuitry 100 key the transmit oscillator 102 ON. The 175 kHz oscillation signal is passed through a transmit output control circuit 104 which operates the transmit output driver 106. The transmit output driver 106 is a Class C driver which drives the dual antenna coils in a parallel aiding configuration to generate a strong H field output. The ON time/DC limit block 100 protects the downstream components of the transmitter from being damaged in the event that an invalid steady state XMITTLM signal is received at terminal J2-8. An input signal remaining high for a predetermined period of time or exceeding a certain duty cycle between input signals is blocked from triggering the transmit oscillator 102.

When triggered by a proper XMITTLM input signal, transmit oscillator block 102 provides a 175 kHz signal to the transmit output control 104 which produces controlled pulse width signals (at fixed 5.71 microsecond pulse intervals) which are applied to the transmit output driver 106 which in turn synchronously excites the parallel resonant antenna L-C tuned circuit, formed by antennae LA and LB and capacitor C44 of FIG. 4A. The current developed in the dual coil circuit generates the 175 kHz sine wave, magnetic field, downlink telemetry. The intervals between bursts define the pulse interval or position modulated data transmitted to the implanted device.

The transmit sense coil 110 situated within the programming head picks up the magnetic field of the transmission output driver circuit 106 and dual coil 108 and generates a XMIT sense signal and applies it to a block 112 as described in the above-incorporated '871 patent. One output of the transmit detection/feedback block 112 is applied to a transmit confirmation comparator output driver 114 which in turn supplies a transmit confirmation signal (XMITCNF) out pin J2-9 to the programmer 26 to confirm the telemetry out of a XMITTLM command. The transmit sense coil 110 receives a portion of the signal which is fed back to a XMIT detection circuit 112 which develops feedback signal applied to transmit output control 104. The output control circuit 104 controls the efficiency of the transmit output driver 106 and compensates for variations due to power supply changes, components, and also load conditions that are presented to the dual antennae coil block 108 due to varying locations of the implanted pulse generator below the patient's skin In FIG. 3, the aspect of the description of particular interest to the present invention is contained within the comparator output driver block 134 of the receiver section in conjunction with the remaining components of the receiver section. Consequently, the transmitter section and the XMIT detection blocks 112 and 114 are not further described herein and reference is made to the above-incorporated '871 patent for a complete disclosure of an example thereof and explanation of the related circuit components depicted in FIGS. 4A–4C.

The dual antenna coil block 108 is coupled with the receiver section comprising circuitry blocks 116, 118, 120, 124, 130, 132 and 134 employed in telemetry uplink transmissions in the uplink telemetry mode. The receiver section processes any detectable uplink telemetry signals present when the downlink telemetry section is not transmitting in the downlink telemetry mode. A receiver gain control signal (RGCTRL) applied via terminal J2-10 or the receiver automatic gain control signal developed by block 132 are employed to set the receiver gain in block 118 in a fashion to be described in greater detail later.

The dual antenna coil block 108 is configured in the same fashion as the antenna coils 22, 24 and diodes 34, 36, 38 and 40 of the '532 patent and operates as described therein as a programmer telemetry antenna tuned circuit that is adapted to be driven into oscillation to generate tuned circuit output signals in response to telemetry uplink transmissions of telemetry uplink signals. The tuned circuit is also susceptible to and responds to electrical noise, e.g., ambient noise and circuit component noise, whereby the tuned circuit output signals can exhibit noise artifacts due to contamination by such electrical noise.

The dual coils $L_A$ and $L_B$ of block 108 (shown in FIG. 4A) operate in a series opposing configuration and are coupled to tuning capacitors in receiver input tuning/buffer block 116 such that the tuned circuit is resonantly tuned to 128 kHz, well outside the 175±25 kHz frequency of interest of the telemetered, RF signal. Consequently, the tuned circuit will "ring", in response to a transient signal well outside the bandpass characteristics of the receiver detector block 124. In effect, the receiver detector 124 is blind to such signals as described in the above-incorporated '871 patent.

The filtered output signal of the block 116 is applied to the receiver gain control block 118 which amplifies the signal as a function of the gain mode and value applied thereto by block 120 applies the amplified output signal to the receiver detector block 124. The receiver gain operating level of receiver gain control block 118 is controllable in two modes referred to as automatic gain control (AGC) and manual gain control mode (MGC). The gain control mode is controlled by the value of the receiver gain control signal (RGCTRL)

delivered by the programmer at the RGCTRL terminal (J2-10). Signal RGCTRL can either be zero microamps, causing the gain control block 118 to operate in the AGC mode, or a DC current level in microamps causing the gain control block 118 to operate in the MGC mode. When operating in the MGC mode, the receiver gain is controlled by the DC current level.

The receiver detector block 124 includes the receiver phase filter 126 and receiver mixer 128. The receiver phase filter 126 effects no phase shift for incoming signals of interest, and up to ±180° of phase shift to signals outside the frequency band of interest and applies it to one input of the receiver mixer 128. The receiver mixer 128 receives the original signal at its other input, and a DC output signal is produced with an amplitude and polarity which is a function of frequency as the two signals are mixed. Signals outside of the range of interest centered at 175 kHz produce a positive going response at the output of detector block 124. Signals within the frequency range of interest between 150 to 208 kHz produce a negative going response at the output of detector block 124. Signals of interest at 175±12.5 kHz are amplified with up to a 30 decibel gain.

The DC output signal of detector block 124 is applied to the input of the receiver carrier filter 130 which demodulates the signal providing the demodulated uplink signal at TP7. The demodulated envelope of the uplink signal (shown in FIG. 5 of the above-incorporated '871 patent) is applied to the input of the receiver comparator output driver 134. In the receiver comparator output driver 134, the demodulated signal is compared against a reference signal that adapts to noise in the demodulated signal itself to develop a limited rise time and fall time, square wave, RCVTLM signal at its output as described further below. The high level output signal RCVTLM at terminal J2-7 is conducted via the cable 24 to the programmer 26.

The output signal of the receiver carrier filter block 130 is also applied to the input of the receiver AGC block 132 which develops the AGC signal value for controlling the gain of the receiver control amplifier 118. As stated above, the AGC signal or the MGC RGCTRL signal is applied to the receiver gain control 118 depending on the state of the receiver AGC/MGC switching block 120.

Returning to the receiver detector 124, it effects a reject band outside a 148–208 kHz range. Therefore, the receiver antennae coils $L_A$ and $L_B$ are tuned in conjunction with capacitors in the receiver input tuning/buffer block 116 below 150 kHz with a Q still high enough to allow reasonable amplitude response at 175 kHz. Transient noise exciting the tuned circuit produces a ringing noise response at the tuned frequency, and the noise response stimulates the detector 124 to produce a desired inverted output signal. As the transient noise amplitude increases, the inverted output signal increases in amplitude, driving the detector 124 output level further away from the trigger level of the post detection comparator block 134. Any steady state noise signal in the reject band will also result in a steady state inverted detector 124 response which will not trigger the comparator output driver 134 in the absence of a sufficiently strong signal within the frequency range of interest.

Turning now to FIGS. 4A–4C, they depict one form of a transceiver circuit in a programming head in which the present invention may be implemented. However, it will be understood that the present invention can be employed in other receiver sections of such transceiver circuits, and that the specifically described and depicted blocks of this exemplary receiver section can be modified in many respects. The present invention is realized in the final comparator block 134 of the transceiver section, and the receiver section blocks between the dual coil block 108 and the comparator block 134 can be modified in many respects to enable the reception and demodulation of RF telemetry signals that are encoded in the varieties of ways described above and having differing amplitudes and characteristics:

Receiver Input Circuitry 116: The receiver input circuitry 116 involves the portion of the schematic of FIG. 4A from the antenna coils LA and LB, connected in a series opposing configuration for uplink telemetry reception, to TP2. In the receive mode, diodes CR1, CR2, CR11, and CR17 of the receiver input circuitry 116 remain non-conducting, thereby providing isolation of the receiver input from the transmitter section circuitry. Using the net mutual inductance of $L_A$ and $L_B$, the receiver input circuitry 116 is tuned with capacitors C1, C2 and resistor R1 in parallel with the input impedance of the U2 buffer circuit. The receiver input circuitry 116 is thereby tuned to approximately 128 kHz even though the signal of interest at the receiver is 175 kHz. Differential amplifier U1 buffers the input and provides approximately 15 dB gain.

There are various guard tracks as indicated on the schematic (U1, U2 guard track) that connect to the antennae E-shield that is described in greater detail in the above-incorporated '871 patent. These guard tracks improve isolation between the sensitive receiver input circuitry 116 and other close by circuit components.

Amplifier U1 is heavily decoupled from the power supply to provide a good margin of power supply isolation.

Receiver Gain Control Circuitry 118: The receiver gain control circuitry 118 shown in FIG. 4A commencing at test point TP2 utilizes an OTA (operational transconductance amplifier) designated as U2 and an operational amplifier (op amp) U3 configured as a unity gain buffer to drive the detector input signal at TP6 (FIG. 4B-1). The gain of OTA U2 is controlled by the current into pin 5 which is supplied from the AGC circuitry 120 and 132 explained hereafter in reference to FIGS. 4A, 4B-1 and 4B-2.

Receiver Detector Circuitry 124 (Blocks 126 and 128): The receiver detector circuitry 124 comprises the receiver phase shifting filter circuitry 126 shown in FIGS. 4B-1 and 4B-2 and the active mixer circuitry 128 shown in FIG. 4B-1. The receiver detector circuitry 124 processes the detector input signal at TP6 in an unbalanced fashion and mixes it with a phase shifted version of the same detector input signal at TP6 to produce a detected negative going DC component at U7-6 which is a function of frequency. The DC response emulates a system having a narrow 25 kHz bandpass filter operating at 175 kHz, but does not share the same degree of undesirable transient response associated with such narrow filters. For signals in the reject band, the output at U7-6 is a signal of opposite polarity to the desired signal polarity. The phase shifting filter circuitry 126 and the active mixer circuitry 128, in conjunction with the design of the receiver input circuitry 116, produces a very selective detector for signals within the desired pass band while providing a high level of rejection for both transient noise and out-of band steady state noise.

This combination provides level signal rectification, precise narrow bandpass filtering, as well as 30 dB amplification. The only calibration required is an offset calibration controlled by resistor R39 shown in FIG. 4B-1.

The necessary phase shifting of the detector input signal at TP6 is accomplished by phase shifting filter circuitry 126 with two active bandpass stages comprising amplifier stages U4 and U5 which are identical and each provide 6 dB of gain at 175 kHz. The Q (2.67) of each stage of the phase shift network is designed to produce the correct amount of phase shifting necessary to yield the simulated 25 kHz bandpass filter characteristic after the mixing process accomplished by the mixer circuitry 128. The phase shifting filters (U4, U5 and associated components) are constructed with one percent metal film resistors and NPO capacitors for the necessary temperature stability. The filter op amps U4, U5 (Motorola MC34081) were selected for their high gain band width product for the operating supply current required. The finite open loop gain of the op amps U4, U5 is low enough to require compensation to achieve the precision necessary to avoid calibration. This compensation is accomplished by using a center frequency design value shifted by the same percentage as the theoretical open loop phase error expected for this op amp. The output of the phase shifting filter circuitry 126 amplified by a total of 12 dB (at 175 kHz) is then presented to the input of the U6 mixer in an unbalanced mode.

The mixing process at U6 of the active mixer circuitry 128 provides approximately 30 dB of gain and yields a signal having twice the frequency of the input signal. Additional gain of approximately 6 dB is provided by the U7 output buffer. The 175 kHz signal of interest is not phase shifted by the phase shifting filter circuitry 126, and when it is mixed with the input signal at TP6 results in a rectified signal at U7-6 with a DC component going in the negative direction. Signals above and below 175 kHz are shifted either positive or negative, producing a mixing result yielding a lower amplitude signal at U7-6. For signals below 148 kHz and above 208 kHz, the phase shifting is sufficient enough to produce a positive going signal at U7-6.

This detection process combined with the receiver input coil transient characteristics provides a transient noise immunity as follows. Transient noise pulses in either the H or E field mode exciting the input coils $L_A$ and $L_B$ results in a natural resonant frequency ringing of the input tuned frequency, i.e., 128 kHz. This signal is amplified in a wide band fashion and presented to TP6. The 128 kHz noise at TP6 is phase shifted sufficiently enough by the phase shifting filter circuitry 126 so as to produce a positive going result at the detector output U7-6. For the case of steady state noise signals that are outside the 148–208 kHz band, the result is a steady state positive DC offset at U7-6. In both cases, the response at U7-6 serves to diminish noise signal levels with respect to uplink telemetry signal levels, thereby reducing the threat of a false positive response to noise.

It should be noted that these described functions of the receiver phase shifting filter circuitry 126 and the active mixer circuitry 128 can be implemented in a software or firmware manner in a digital signal processor (DSP) having the capacity to process RF telemetry signals that are encoded in a variety of manners.

Carrier Filter Circuitry 130: The detector output signal of op amp U7 is applied to and processed by the carrier filter circuitry 130 comprising op amp U8 and associated circuitry shown in FIG. 4B-2 to produce the demodulated uplink pulse at TP7 when op amp U8 is not blanked by the XMITTLM signal. The carrier filter 130 is a 16 kHz low pass filter with dampening coefficient of 0.6, and the filter design yields a high level of carrier ejection without introducing excessive group delay distortion. The MC34081 op amp U8 provides good filter behavior to 500 kHz. It will be understood that the carrier filtering function can also alternatively be carried out in a software or firmware implementation employing a DSP.

An analog switch U11-1 is normally open, but is closed by the XMITTLM signal coupled through resistors R42 and R44 to blank the op amp U8 during downlink telemetry transmissions to prevent unwanted RCVTLM pulses at the output J2-7. The output of the carrier filter op amp U8 is buffered with some amplification by the op amp U9-1 and provides a positive going signal at TP7.

The receiver shutdown during the XMITTLM signal is controlled by the dual monostable component U10 and associate circuitry in FIG. 4B-2. Both monostables in component U10 are triggered ON by the XMITTLM signal applied to U10-5 and U10-12 respectively. One monostable is set to be triggered ON for slightly under 1.0 msec, and its output at U10-6 is applied through diode CR5 to close switch U11-1. Resistor R44 and diode CR5 provide additional shutdown so that when the XMITTLM signal goes high, U11-1 will close, grounding the demodulator op amp U8 for 1.0 msec after the XMITTLM signal goes low, thereby providing a 1.0 msec blanking interval after the transmit operation. This blanking interval is sufficient to prevent any false artifacts from being generated on the RCVTLM line due to the MITTLM signal.

Receiver Gain Control Circuitry 132, 120: As described above, the gain of OTA U2 of the receiver gain control circuitry 118 can be controlled in either the AGC mode or the MGC mode, depending on the current level of the receiver gain control line (RGCTRL), which is manually input by the user. The current level on RGCTRL is set to zero (i.e., <5 microamps) to operate in AGC mode or is set to a current level between 20 microamps to one milliampere to operate and control gain in the MGC modes.

The receiver section AGC circuitry 132 is depicted in FIGS. 4B-1 and 4B-2 and is achieved with a second order feedback network that operates from peak detection of the demodulated signal at TP7 applied to capacitor C32 through diode CR4 and resistor R53. The advantage of attempting a second order AGC design is that assessing the stability of the device is simplified. Since the received signal is not a steady state signal but a transitory signal, the sampling process for the AGC must be done in such a fashion so as to compensate for the duty cycle. This is done by inversely controlling the charge and discharge of the sampling capacitor C32 so as to compensate for the duty cycle. The two poles associated with the second order feedback network are created by the sampling capacitor C32 network and the integrator op amp U12-2. When properly achieved, the DC voltage capacitor of capacitor C32 should equal approximately one-half the amplitude of the peak signal level of the detector output signal at TP7.

The DC voltage level on capacitor C32 is maintained during the XMITTLM signal through the operation of the second monostable in dual monostable component U10 which goes ON for 30.0 msec and applies a signal at U10-9 to open switches U11-4 and U11-2. As mentioned before, these two monostables freeze the AGC circuit current level to its operating level prior to transmission. The 30.0 msec interval is set based on current downlink telemetry formats so that the receiver GC will be maintained at its level prior to the beginning of the transmission between transmit blocks when no XMITTLM pulses occur. Following the 30 millisecond time-out, the U11-9 and U11-8 switches are closed, and the AGC circuitry 132 is allowed to integrate the detector signal level at TP7.

At other times in the receive mode, a proportional sample of the net resulting voltage on capacitor C32 is sampled and buffered by op amp U12-1. This output signal of op amp U12-1 is then integrated in an integrator op amp U12-2, which produces a driving current signal level for the OTA U2 of the receiver gain circuitry 118.

Receiver AGC/MGC switching circuitry 120 comprises op amp U9-2 and a third switch U11-3 and that responds to a signal at U11-16 to open or disconnect the AGC output circuit to allow manual gain control of the OTA U2 via the RGCTRL signal level input from the programmer. Op amp U9-2 is used as a switch to detect when the programmer is sending a current pulse of sufficient duration to switch to the MGC mode by opening switch U11-3 at terminal U11-16. AGC operation is guaranteed for current levels on the RGCTRL input from 0 to 5 microamps. The switching process occurs between 5 and about 10 microamps, and sufficient receiver gain for normal operation is achieved over the range of 20 microamps to one milliampere. The MGC mode current is conducted through diodes CR6, CR7 and CR8 and bypasses switch U11-3. Diodes CR18 and CR19 (FIG. 4A) simulate diode junctions as seen into pin 5 of OTA U2, thereby providing easier design of the current divider created by resistors R62 and R72.

Output Comparator Circuitry 134: The demodulated signal at TP7, with a typical peak amplitude of 5 volts, is coupled to the output comparator circuitry 134 comprising differential amp U39-1 and its associated filter and feedback components. As described above, the receiver section detects and demodulates the telemetry uplink signals from the tuned circuit output signals and provides a demodulated, analog, uplink signal at TP7 having a demodulated uplink signal amplitude that varies with time as a function of telemetry uplink signal amplitude variations and noise artifacts, including electrical interference and low frequency components associated with patient movement.

The improved adaptive comparator circuitry 134 of the present invention is formed by an op amp U39 that compares the demodulated uplink signal amplitude at TP7 applied to its positive input with an adaptive threshold signal applied to its negative input and provides a receiver output signal at its output when the demodulated uplink signal amplitude exceeds the adaptive threshold amplitude of the adaptive threshold signal. The comparator circuitry 134 further comprises resistor R122 and capacitor C99 and a Vref DC reference voltage of 1.16 volts in this circuit implementation that may be supplied by a conventional resistor divider network or reference voltage IC coupled to VDD and ground. The values of the reference voltage and the resistor R122 and capacitor C99 are selected to provide high pass filtering with the three dB point at 1562 Hz in order to pass 87.5 kbits/second using the 175 kHz carrier frequency. The threshold amplitude floats just above the noise floor. A feedback resistor R89 and capacitor C217 are coupled between the negative input and the output of op amp U39 limits bandwidth. The op amp U39 is an Analog Devices AD8031 op amp which has a large bandwidth.

Figure 6:
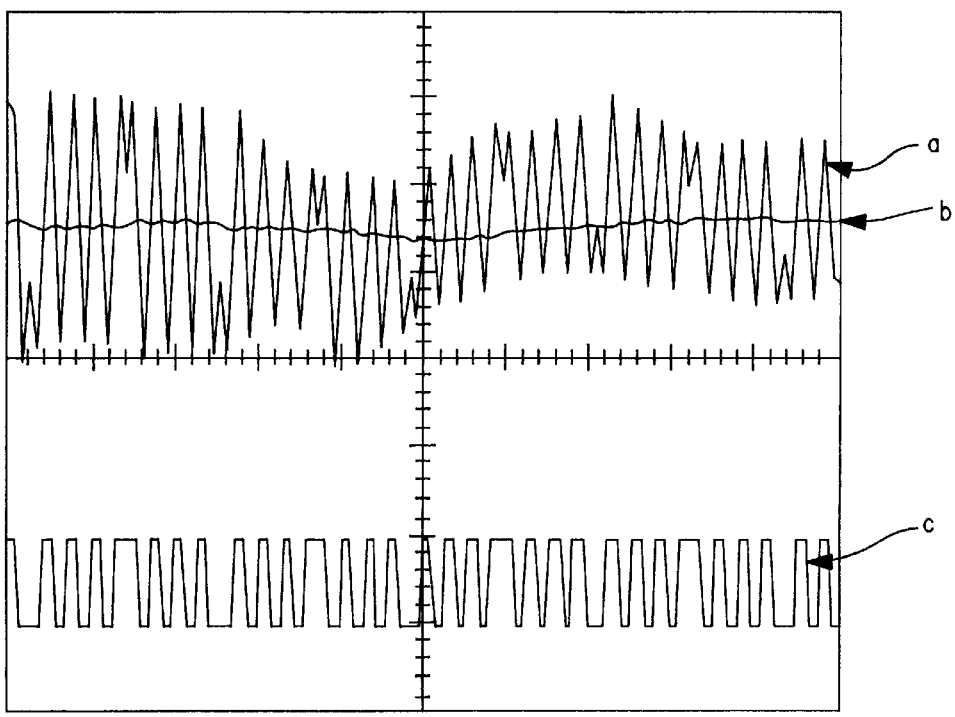
FIG. 6 is a waveform diagram displaying the operation of the adaptive comparator block of FIG. 4B-2 in discriminating uplink telemetry RF signals from noise.

A simulation of the operation of the adaptive comparator 134 is depicted in FIGS. 5 and 6 wherein the upper tracings (a) and (b) depict the input signal and the adaptive reference signal applied to the positive and negative input terminals of the op amp C39, and tracing (c) depicts the squared receiver output signal of the op amp C39 in each case. In these depictions, the input signal is modulated using a PSK encoding scheme to provide the 87.5 kbits/second data capacity, and the circuit response is at these points is displayed on the screen of a TDS 784 digital oscilloscope. The voltage reference Vref is not imposed on the adaptive filter in this simulation.

In FIGS. 5 and 6, the tracings (a) and (b) illustrate the input and reference signals without noise and with noise. In each case, the carrier in tracing (a) is shown not modulated in the left portion of the tracings and is shown modulated using PSK encoding in the right portions of the tracings. The adaptive reference illustrated in tracing (b) of FIG. 5 is relatively flat, whereas it is modulated by the imposed noise in tracing (b) of FIG. 6. In FIG. 6, low frequency noise that is typically well below the 1562 Hz filter pole, e.g., 60 Hz mains frequency, is imposed on the input signal of tracing (a), but it cannot be seen directly on the display of FIG. 5 because the TDS oscilloscope does not have a screen of sufficient size and resolution to display the noise and the input signals at the 175 kHz carrier frequency at the same time. However, the influence of the noise can be seen in the adaptive reference signal of tracing (b) of FIG. 6.

Thus, the demodulated uplink signal amplitude at TP7 applied to its positive input of op amp U39 is compared to the high pass filtered demodulated uplink signal amplitude applied to the negative input of op amp U39 which and provides the receiver output signal at its output terminal. As shown in tracing (c) of FIGS. 5 and 6, the output signal of the op amp U39 is a square wave having a fixed amplitude and a duration that commences when the rising demodulated uplink signal amplitude exceeds the adaptive threshold and terminates when the falling demodulated uplink signal amplitude falls below the adaptive threshold. There is no output signal from the op amp U39 during other times because the noise artifact amplitude in the demodulated uplink signal applied to the positive input of op amp 39 does not exceed the noise artifact amplitude component of the adaptive threshold amplitude.

The adaptive threshold function enables the threshold to closely track the noise and provide 2–3 dB greater signal-to-noise protection. It is of particular advantage when used with a variety of signal encoding schemes, e.g., FM and AM, PSK, FSK, BPSK, ASK, PPM, and PIM encoding schemes when communicating with an IMD. Typically, IMDs the gate count of CMOS IC components are limited to conserve space and power, and the implementations of the various encoding schemes are imperfectly realized. For example, the PSK modulated uplink signal can have a parasitic AM component, and the uplink signal amplitude tends to vary.

Although the preferred embodiments of the present invention have been described in the context of a Medtronic programming system, it will be appreciated that the following claims are not so limited or confined but are instead applicable to programming or telemetry systems of any manufacturer for any IMD or implant. Those of skill in the art will be readily able to apply the teaching found herein to yet other embodiments within the scope of the following claims.

Although particular embodiments of the invention have been described herein in some detail, this has been done for the purpose of providing a written description of the invention in an enabling manner and to form a basis for establishing equivalents to structure and method steps not specifically described or listed. It is contemplated by the inventors that the scope of the limitations of the following claims encompasses the described embodiments and equivalents thereto now known and coming into existence during the term of the patent. Thus, it is expected that various changes, alterations, or modifications may be made to the invention as described herein without departing from the spirit and scope of the invention as defined by the appended claims.

What is claimed is:

1. An external programmer for receiving information-encoded, telemetry uplink signals transmitted from an implantable medical device (IMD) telemetry antenna and transmitter circuit in an IMD in a telemetry uplink transmission, said external programmer comprising:

a programmer telemetry antenna tuned circuit comprising at least one antenna coil and at least one tuning capacitor, the programmer telemetry tuned circuit adapted to be driven into oscillation to generate tuned circuit output signals in response to telemetry uplink transmissions of telemetry uplink signals and in response to electrical noise, whereby the tuned circuit output signals can exhibit noise artifacts due to contamination by such electrical noise;

a telemetry receiver section for detecting and demodulating the telemetry uplink signals from the tuned circuit output signals and providing a demodulated uplink signal having a demodulated uplink signal amplitude that varies with time as a function of telemetry uplink signal amplitudes and noise artifacts;

an adaptive comparator circuit for comparing the demodulated uplink signal amplitude with an adaptive threshold signal and providing a receiver output signal when the demodulated uplink signal amplitude exceeds the adaptive threshold amplitude of the adaptive threshold signal, the comparator circuit further comprising means for filtering and integrating the demodulated uplink signal to derive an adaptive threshold amplitude that is proportional to and adapts to the amplitude of noise artifacts in the demodulated uplink signal; and comparison means having a first input terminal for receiving the demodulated uplink signal and a second input terminal for receiving the adaptive threshold signal and an output terminal for comparing the demodulated uplink signal amplitude with the adaptive threshold amplitude and providing the receiver output signal at the output terminal only when the telemetry signal amplitude in the demodulated uplink signal exceeds the adaptive threshold amplitude.

2. The programmer of claim 1, wherein said telemetry receiver section further comprises an RF telemetry receiver section further comprising:

means for amplifying RF signals induced within said tuned circuit and providing an amplified RF signal;

means responsive to said amplified RF signal for shifting its phase and for providing a phase shifted, amplified RF signal; and means for mixing said phase shifted, amplified RF signal with said amplified RF signal for providing a monophasic component of said mixed RF amplified signal, the amplitude of which is a function of frequency; and means for demodulating said monophasic component of said mixed RF amplified signal for providing a detected DC component of said RF amplified signal.

3. The programmer of claim 2, wherein said tuned circuit resonates outside a bandpass frequency range containing said received data signals.

4. The programmer of claim 2, wherein said monophasic component of said mixed amplified RF signal has a first polarity for said amplified RF signals within a bandpass frequency range containing said received data signals and a second polarity for said amplified RF signals outside said bandpass frequency range.

5. The programmer of claim 2, wherein the information-encoded, telemetry uplink signals transmitted from an IMD telemetry antenna and transmitter circuit in an IMD in a telemetry uplink transmission are encoded via one of the encoding schemes selected from the group consisting of FM, AM, phase shift keying (PSK), frequency shift keying (FSK), biphasic frequency shift keying (BPSK) amplitude shift keying (ASK), pulse position modulation (PPM), and pulse interval modulation (PIM).

6. The programmer of claim 1, wherein the information-encoded, telemetry uplink signals transmitted from an IMD telemetry antenna and transmitter circuit in an IMD in a telemetry uplink transmission are encoded via one of the encoding schemes selected from the group consisting of FM, AM, phase shift keying (PSK), frequency shift keying (FSK), biphasic frequency shift keying (BPSK) amplitude shift keying (ASK), pulse position modulation (PPM), and pulse interval modulation (PIM).

7. The programmer of claim 1, wherein the comparison means further comprises:

an op amp having first and second input terminals and an output terminal;

means for applying the demodulated signal to the first input terminal of the op amp; and means for applying the adaptive threshold signal to the second input terminal of the op amp, whereby the receiver output signal at the output terminal of the op amp comprises the difference between the demodulated signal amplitude and the adaptive threshold amplitude.

8. A telemetry system for receiving information-encoded, telemetry signals transmitted from one of an implantable medical device (IMD) or an external programmer to the other of the external programmer or IMD employing a telemetry antenna and transmitter circuit in a telemetry transmission, wherein each of said IMD of said external programmer comprises:

a telemetry antenna tuned circuit comprising at least one antenna coil and at least one tuning capacitor, the telemetry tuned circuit adapted to be driven into oscillation to generate tuned circuit output signals in response to telemetry transmissions of telemetry signals and in response to electrical noise, whereby the tuned circuit output signals can exhibit noise artifacts due to contamination by such electrical noise;

a telemetry receiver section for detecting and demodulating the telemetry signals from the tuned circuit output signals and providing a demodulated signal having a demodulated signal amplitude that varies with time as a function of telemetry signal amplitudes and noise artifacts;

an adaptive comparator circuit for comparing the demodulated signal amplitude with the threshold amplitude of an adaptive threshold signal and providing a receiver output signal when the demodulated signal amplitude exceeds the adaptive threshold amplitude of the adaptive threshold signal, the comparator circuit further comprising means for filtering and integrating the demodulated signal to derive an adaptive threshold amplitude that is proportional to and adapts to the amplitude of noise artifacts in the demodulated signal; and comparison means having a first input terminal for receiving the demodulated signal and a second input terminal for receiving the adaptive threshold signal and an output terminal for comparing the demodulated signal amplitude with the adaptive threshold amplitude and providing the receiver output signal at the output terminal only when the demodulated signal amplitude exceeds the adaptive threshold amplitude.

9. The system of claim 8, wherein the information-encoded, telemetry signals transmitted from a telemetry antenna and transmitter circuit in a telemetry transmission are encoded via one of the encoding schemes selected from the group consisting of FM, AM, phase shift keying (PSK), frequency shift keying (FSK), biphasic frequency shift keying (BPSK) amplitude shift keying (ASK), pulse position modulation (PPM), and pulse interval modulation (PIM).

10. The system of claim 8, wherein the comparison means further comprises:

an op amp having first and second input terminals and an output terminal;

means for applying the demodulated signal to the first input terminal of the op amp; and means for applying the adaptive threshold signal to the second input terminal of the op amp, whereby the receiver output signal at the output terminal of the op amp comprises the difference between the demodulated signal amplitude and the adaptive threshold amplitude.

11. A method of receiving information-encoded, telemetry signals transmitted from one of an implantable medical device (IMD) or an external programmer to the other of the external programmer or IMD employing a telemetry antenna and transmitter circuit in a telemetry transmission, wherein each of said IMD or said external programmer comprises:

a telemetry antenna tuned circuit comprising at least one antenna coil and at least one tuning capacitor, the telemetry tuned circuit adapted to be driven into oscillation to generate tuned circuit output signals in response to telemetry transmissions of telemetry signals and in response to electrical noise, whereby the tuned circuit output signals can exhibit noise artifacts due to contamination by such electrical noise; and a telemetry receiver section for detecting and demodulating the telemetry signals from the tuned circuit output signals and providing a demodulated signal having a demodulated signal amplitude that varies with time as a function of telemetry signal amplitudes and noise artifacts; the method comprising the steps of:

filtering and integrating the demodulated signal to derive an adaptive threshold signal having an adaptive threshold amplitude that is proportional to and adapts to the amplitude of noise artifacts in the demodulated signal; and comparing the demodulated signal amplitude with the adaptive threshold amplitude and providing a receiver output signal when the demodulated signal amplitude exceeds the adaptive threshold amplitude of the adaptive threshold signal.

12. The method of claim 11, wherein the comparing step further comprises the steps of:

providing an op amp having first and second input terminals and an output terminal;

applying the demodulated signal to the first input terminal of the op amp; and applying the adaptive threshold signal to the second input terminal of the op amp, whereby the receiver output signal at the output terminal of the op amp comprises the difference between the demodulated signal amplitude and the adaptive threshold amplitude.

13. The method of claim 12, wherein the information-encoded, telemetry signals transmitted in a telemetry transmission are encoded via one of the encoding schemes selected from the group consisting of FM, AM, phase shift keying (PSK), frequency shift keying (FSK), biphasic frequency shift keying (BPSK) amplitude shift keying (ASK), pulse position modulation (PPM), and pulse interval modulation (PIM).

14. The method of claim 11, wherein the information-encoded, telemetry signals transmitted in a telemetry transmission are encoded via one of the encoding schemes selected from the group consisting of FM, AM, phase shift keying (PSK), frequency shift keying (FSK), biphasic frequency shift keying (BPSK) amplitude shift keying (ASK), pulse position modulation (PPM), and pulse interval modulation (PIM).

15. In a telemetry receiver for receiving information-encoded, telemetry signals transmitted from one of an implantable medical device (IMD) or an external programmer to the other of the external programmer or IMD employing a telemetry antenna and transmitter circuit in a telemetry transmission, wherein the receiver further comprises:

a telemetry antenna tuned circuit comprising at least one antenna coil and at least one tuning capacitor, the telemetry antenna tuned circuit adapted to be driven into oscillation to generate tuned circuit output signals in response to telemetry transmissions of telemetry signals and in response to electrical noise, whereby the tuned circuit output signals can exhibit noise artifacts due to contamination by such electrical noise;

a telemetry receiver section coupled to the telemetry antenna to detect and to demodulate the telemetry signals from the tuned circuit output signals and to provide a demodulated signal having demodulated signal amplitude that varies with time as a function of telemetry signal amplitudes; and an adaptive comparator circuit coupled to the telemetry receiver section to receive the demodulated signal, to generate an adaptive threshold signal indicative of a level of the electric noise in the demodulated signal, and to provide a filtered receiver output signal when the adaptive threshold signal has a predetermined relationship to the demodulated signal.

16. The receiver of claim 15, wherein the comparison means further comprises:

an op amp having first and second input terminals and an output terminal;

means for applying the demodulated signal to the first input terminal of the op amp; and means for applying the adaptive threshold signal to the second input terminal of the op amp, whereby the receiver output signal at the output terminal of the op amp comprises the difference between the demodulated signal amplitude and the amplitude of the adaptive threshold signal.

17. The receiver of claim 16, wherein the information-encoded, telemetry signals transmitted in a telemetry transmission are encoded via one of the encoding schemes of the group consisting of FM, AM, phase shift keying (PSK), frequency shift keying (FSK), biphasic frequency shift keying (BPSK) amplitude shift keying (ASK), pulse position modulation (PPM), and pulse interval modulation (PIM).

18. The receiver of claim 15, where in the information-encoded, telemetry signals transmitted in a telemetry transmission are encoded via one of the encoding schemes of the group consisting of FM, AM, phase shift keying (PSK), frequency shift keying (FSK), biphasic frequency shift keying (BPSK) amplitude shift keying (ASK), pulse position modulation (PPM), and pulse interval modulation (PIM).

* * * * *